(12) United States Patent
Patterson et al.

(10) Patent No.: US 12,181,381 B2
(45) Date of Patent: Dec. 31, 2024

(54) BIOLOGICAL SAMPLE RECEIVERS

(71) Applicant: QIAGEN Healthcare Biotechnologies Systems GmbH, Hilden (DE)

(72) Inventors: Anthony Richard Patterson, Cardiff (GB); Anthony Carl Williams, Cardiff (GB); Paul Slater, Cardiff (GB)

(73) Assignee: QIAGEN HEALTHCARE BIOTECHNOLOGIES SYSTEMS GMBH, Hilden (DE)

( * ) Notice: Subject to any disclaimer, the term of this patent is extended or adjusted under 35 U.S.C. 154(b) by 589 days.

(21) Appl. No.: 16/966,355

(22) PCT Filed: Jan. 10, 2019

(86) PCT No.: PCT/EP2019/050599
§ 371 (c)(1),
(2) Date: Jul. 30, 2020

(87) PCT Pub. No.: WO2019/149501
PCT Pub. Date: Aug. 8, 2019

(65) Prior Publication Data
US 2020/0408646 A1    Dec. 31, 2020

(30) Foreign Application Priority Data
Feb. 1, 2018  (GB) ..................................... 1801691

(51) Int. Cl.
*G01N 1/02*     (2006.01)
*B65D 75/14*    (2006.01)
(Continued)

(52) U.S. Cl.
CPC .............. *G01N 1/02* (2013.01); *B65D 75/14* (2013.01); *B65D 75/54* (2013.01); *G01N 2001/007* (2013.01)

(58) Field of Classification Search
None
See application file for complete search history.

(56) References Cited

U.S. PATENT DOCUMENTS 4,206,844 A * 6/1980 Thukamoto ............ B65D 75/54
                                                    428/34.3
5,496,562 A    3/1996 Burgoyne
(Continued)

FOREIGN PATENT DOCUMENTS

| EP | 3015387 A1 | 5/2016 |
| WO | 96/41182 A1 | 12/1996 |
| WO | 2013/088134 A1 | 6/2013 |

OTHER PUBLICATIONS

The International Search Report issued in PCT/EP2019/050599 dated May 24, 2019.

*Primary Examiner* — Lore R Jarrett
(74) *Attorney, Agent, or Firm* — MEDLER FERRO WOODHOUSE & MILLS PLLC

(57) ABSTRACT

Disclosed is a biological sample receiver (100) comprising: a planar substrate (10) for receiving a biological sample including a surface area (11) for accepting a biological sample; an envelope (25) substantially surrounding the substrate, said envelope including an opening (34) for facilitating the deposit of a biological sample onto said surface area (11); and a protective cover (40,50,60) formed around the envelope said protective cover including a closure panel (60) moveable at least to a first position where the opening (34) of the envelope is at least partially concealed, and to a second position where the opening (34) is exposed at least sufficiently to allow said deposit, the protective cover (40, 50,60) being arranged further to allow the slidable separation of the envelope from the cover; the device being characterised in that said envelope and said cover are formed from a single sheet (15) of folded material.

18 Claims, 5 Drawing Sheets

(51) Int. Cl.
*B65D 75/54* (2006.01)
*G01N 1/00* (2006.01)

(56) References Cited

U.S. PATENT DOCUMENTS

| | | | | |
|---|---|---|---|---|
| 5,747,351 | A | * | 5/1998 | Hemmati ............. G01N 33/558 |
| | | | | 435/7.1 |
| 2006/0018794 | A1 | * | 1/2006 | LaStella ........... G01N 33/54386 |
| | | | | 422/400 |
| 2008/0299010 | A1 | | 12/2008 | Shivji |
| 2010/0047129 | A1 | * | 2/2010 | LaStella ................. G01N 33/80 |
| | | | | 156/227 |

* cited by examiner

BIOLOGICAL SAMPLE RECEIVERS

FIELD OF THE INVENTION

The present invention relates to a biological sample receiver and a method of manufacturing the same.

BACKGROUND OF THE INVENTION

Biological sample storage substrates are known, for example in the form of a sheet material mounted in a stiff card frame, and are therefore known commercially as sample collection cards. These cards are typically used in large numbers during the collection of DNA samples from criminal suspects, or for collecting potential samples from crime scenes, or other forensic work. Other uses include plant and animal sample collection for genetic studies, diagnostic sample collection and biological research. In each case they receive and store biological material, and so can be regarded as biological sample receivers.

For criminal sample collection purposes, it is of the utmost importance that the sample containment area of the card is not inadvertently touched or otherwise contaminated, because such contamination risks spoiling the collected sample and may have repercussions for the credibility of other evidence collected on similar cards. So, one desirable quality of such a sample receiving card is that a lid or cover be used over a sample receipt area before and after a sample is deposited thereon. Commercially available cards are used in large numbers and so their low cost is important. Adding any additional features to a card, for example moveable covers, increases only marginally the cost of manufacture, but even marginal cost increases are not attractive to the customers who buy large numbers of the cards, because they are often government funded and lacking in financial resources. Consequently, low cost exposed surface cards are widely used.

Another issue with known collection cards is that wet-collected samples are best preserved if they are first dried before being placed in sealed (plastic) evidence bags or the like. Since the usual arrangements are a simple flat card, drying racks and the like need to be used prior to bagging, which action adds to the potential contamination risks.

Once away from the crime scene, for example in an automated laboratory, there is less risk of contamination of sample cards because clean laboratory type practices are generally followed. However, there is a need to have an easy to handle sample card, that has no cover or other protection which becomes awkward to deal with in an automated setting.

The inventors have realised that there is a need for a simple low cost biological sample receiver for receiving a biological sample and storing the same after the sample has been collected, that has a good level of protection from contamination before and after a sample is deposited on the receiver, but that can be readily separated from that protection for automated downstream processing. As well as that, it is desirable to keep the production costs of such cards to a minimum.

SUMMARY OF THE INVENTION

The invention provides a biological sample receiver according to claims 1, 9 and 16 having preferred features defined by claims dependent thereon. The invention provides also a sample receiver manufacturing method as defined by claim 12.

Embodiments of the invention address the problems mentioned above by providing a sample receiver, including a sample support medium, which is held in a windowed envelope, which envelope is protected by a removeable cover. The envelope and cover are formed from a single piece of sheet material which keeps costs to a minimum. The once piece construction allows simple manufacture and printing. A weakening of the between the portions of the sheet material which form the envelope, and the portions of the sheet material which form the cover allows ready separability, and as well as providing a tamper evident join.

The invention extends to any combination of features disclosed herein, whether or not those features are mentioned in combination. Further, where two or more features are mentioned in combination, it is intended that such features may be claimed separately without extending the scope of the invention.

BRIEF DESCRIPTION OF THE DRAWINGS

The invention can be put into effect in numerous ways, illustrative embodiments of which are described below with reference to the drawings, wherein.

DETAILED DESCRIPTION OF THE INVENTION

Figure 1:
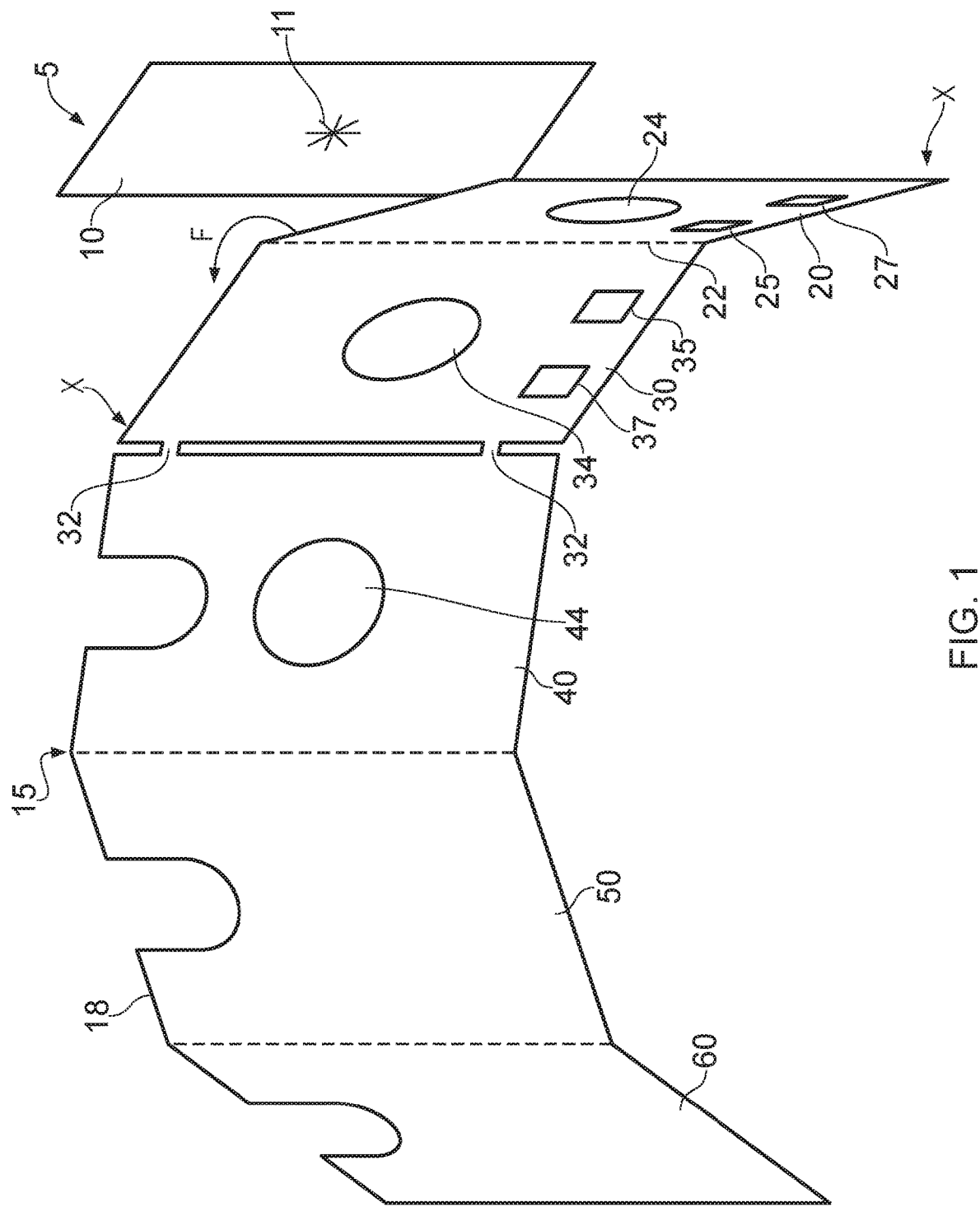
FIG. 1 shows an unfolded view of a biological sample receiver.

The invention, together with its objects and the advantages thereof, may be understood better by reference to the following description taken in conjunction with the accompanying drawings, in which like reference numerals identify like elements in the Figures.

FIG. 1 shows a biological sample storage medium 10 in the form of a planar substrate, for example formed from a piece 5 cut from a larger sheet of material. In this instance, the whole of the surface area of the storage medium 10, provides a solid support for receiving and long term storage of DNA, including blood DNA, which surface includes a compound or composition which protects against significant degradation of DNA incorporated into or absorbed on the surface. In the alternative, just a portion of the piece 5 of the storage medium could be treated to provide against DNA degradation to provide a discrete storage area. In this embodiment, just the surface area 11 on the medium 10 provides a sample receiving area for receiving a biological sample because the remainder of the medium is hidden in use.

The storage medium comprises, for example, a solid support in the form of an absorbent cellulose-based paper, such as filter paper, or a micromesh of synthetic plastics material, with the DNA-protecting compound or composition absorbed onto the solid support. The solid support, or a portion thereof, may treated with a composition consisting essentially of a weak base, a chelating agent, an anionic surfactant or anionic detergent and optionally uric acid or a urate salt, wherein said composition is adsorbed on or incorporated into said paper and allowed to dry to form the sample storage medium 10. In more detail, the solid support, or a portion thereof, may treated with a composition consisting essentially of: (i) ethylene diamine tetra acetic acid; (ii) tris-hydroxymethyl aminomethane; (iii) sodium dodecyl sulphate; and optionally (iv) uric acid or a urate salt, wherein said composition is adsorbed on or incorporated into said support, to provide the storage medium 10. The solid support may be untreated, or may have a different treatment to that mentioned above.

Figure 2:
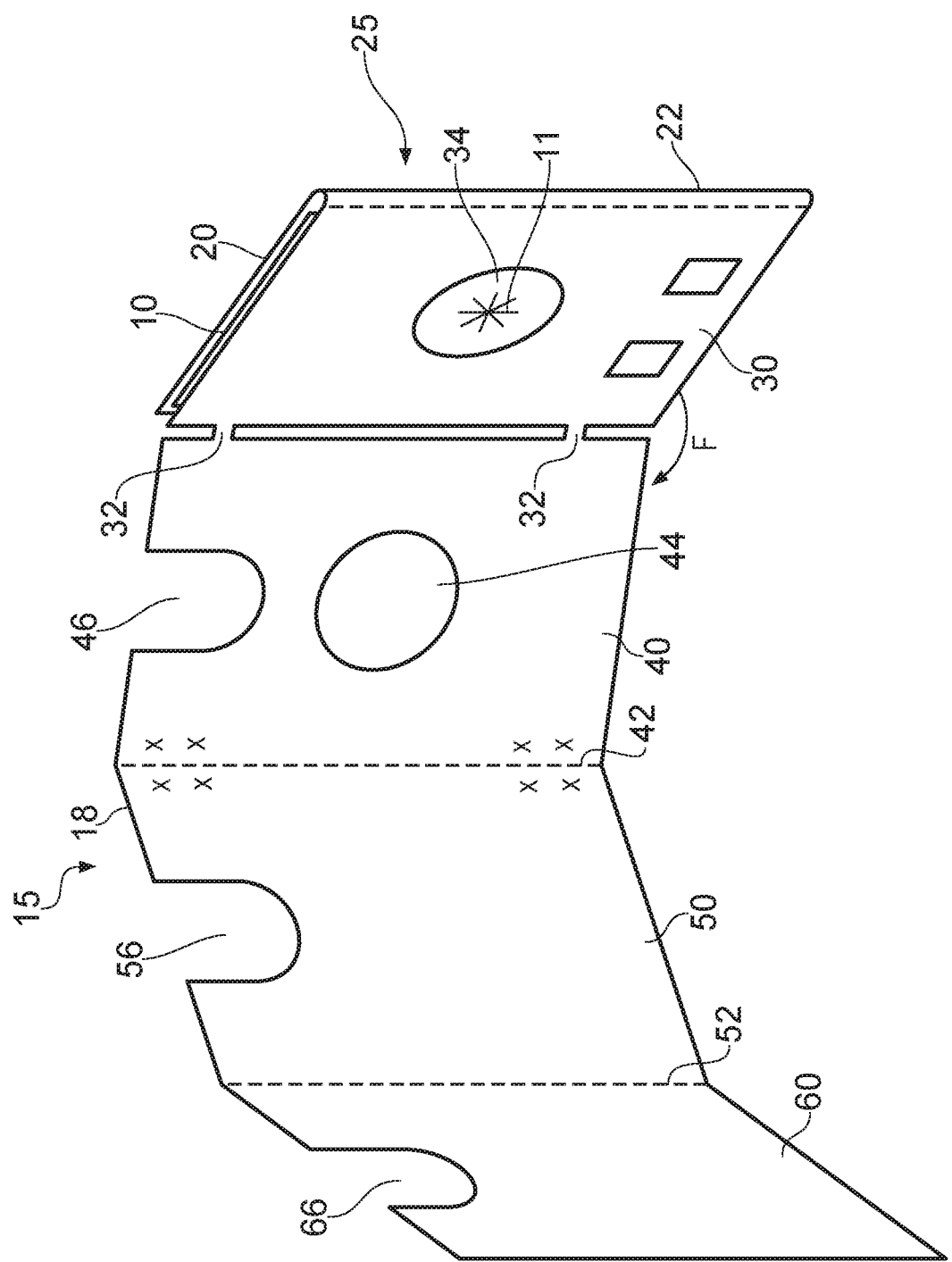
FIGS. 2 to 5 show the same sample receiver as shown in FIG. 1 but in various states of construction.

With reference additionally to FIG. 2, once treated, the storage medium is incorporated into an envelope 25, comprising two opposing panels 20 and 30 formed from one sheet of card material, in this case a blank 15, folded at a fold line 22 in the direction of arrow F and held together by adhesive deposited along glue lines x on the back faces of the panels 20 and 30, as shown in FIG. 1. Thus, an envelope 25 (FIG. 2) is formed around the storage medium 10. It will be noted that openings 24 and 34 are formed in the panels 20 and 30 to provide a window through which a biological sample can be deposited on to the storage medium 10 at a deposit area 11, and through which a portion of the storage medium can be removed, for example by through-punching that portion, facilitated by the two openings being in register when the panels 20 and 30 are folded together.

As further illustrated in FIG. 2, panel 30 is joined by perforations 32, to further panels 40, 50 and 60 formed from the same sheet of material of the blank 15, the further panels 40, 50 and 60 being joined at respective fold lines 42 and 52. Panel 40 includes a further opening 44. In addition, the panels 40,50 and 60 include finger-size cut-outs 46, 56, 66 respectively, along one edge 18 of the blank 15 arranged such that they fold into register.

Figure 3:
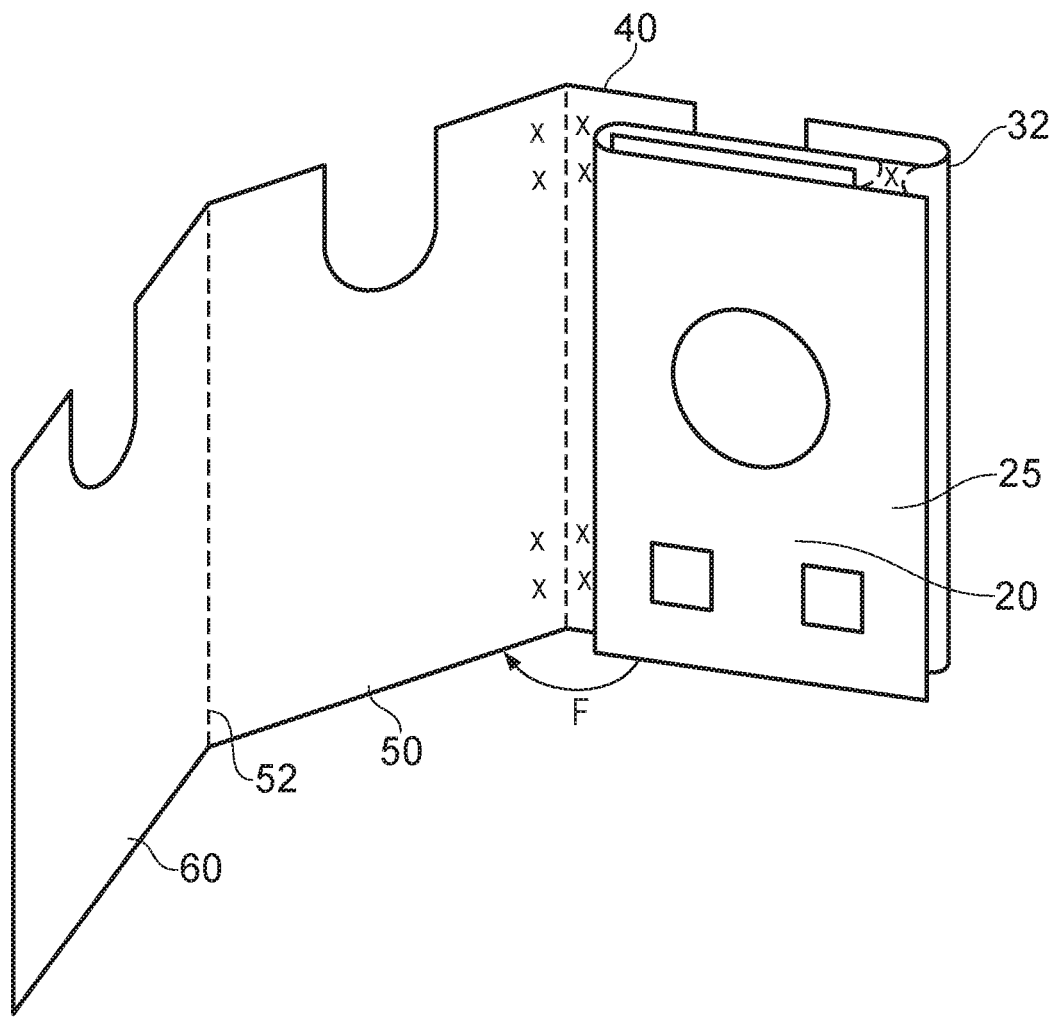
Figure 4:
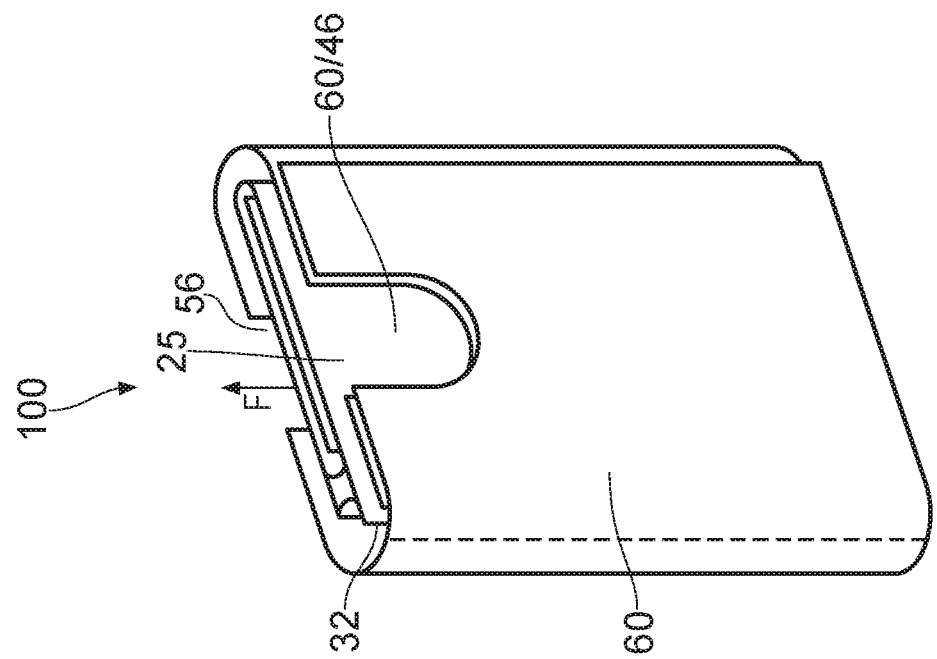
Figure 5:
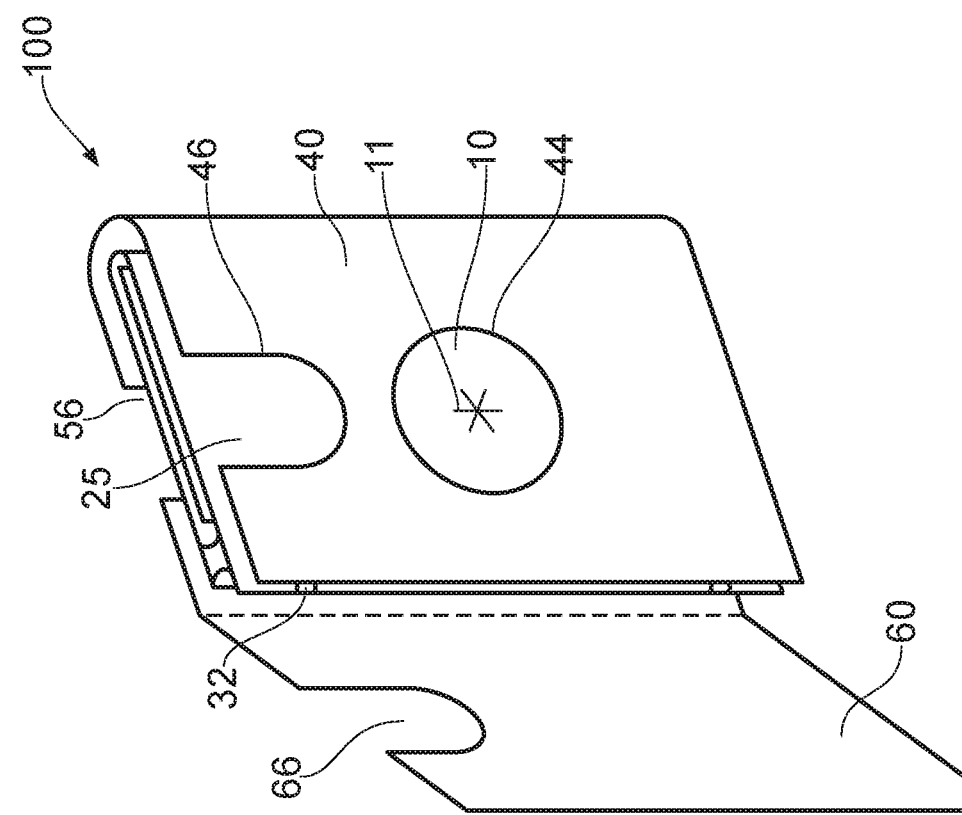

With reference additionally to FIGS. 3 and 4, the envelope 25 is folded onto panel 40 at the perforations 32, and folded yet again at fold line 52 onto panel 50 in the directions of the arrows F shown in FIGS. 2 and 3, and held in place by glue points 'x' shown in FIG. 3 to provide the finished receiver 100 shown in FIGS. 4 and 5. In the finished receiver 100, panel 60 acts as a foldable cover over a sample receiver window 44 at which is exposed the sample receiving area 11 of the sample storage medium 10. A generally closed cover is shown in FIG. 5 and an open cover is shown in FIG. 4.

In use, the receiver 100 is supplied in a closed condition as shown in FIG. 5. The user opens the cover panel 60, and immediately deposits a biological sample onto the area 11, for example using a DNA free swab possibly containing DNA from a crime scene. Once the sample has been deposited on the storage medium through the window 44, and optionally, allowed time to dry, the cover panel 60 is closed.

Later, for example at a forensics laboratory the envelope 25 can be gripped through the aligned cut-outs 46 and 56 between a user's forefinger and thumb, for using automated means. The envelope can be removed readily from the remaining cover panels, because the perforations 32 allow its easy separation, and one edge, edge 18 in this case, of the cover panel portions 40, 50 and 60 of blank 15 is free of glue, which allows the envelope 25 to be slid out of those cover panels in the direction of arrow F in FIG. 5. FIG. 5 also shows the weak perforated connection 32 between the envelope and the other folded panels 40,50 and 60. In practice all that is needed is just two or three uncut joins between panel 40 and panel 30 to keep those parts together until they are pulled apart. Perforations are preferred but any weakness would give satisfactory results, for example a cut partially through the thickness of the sheet material, an abraded region, or a wasted region brought about by heat and/or pressure.

Figure 6:
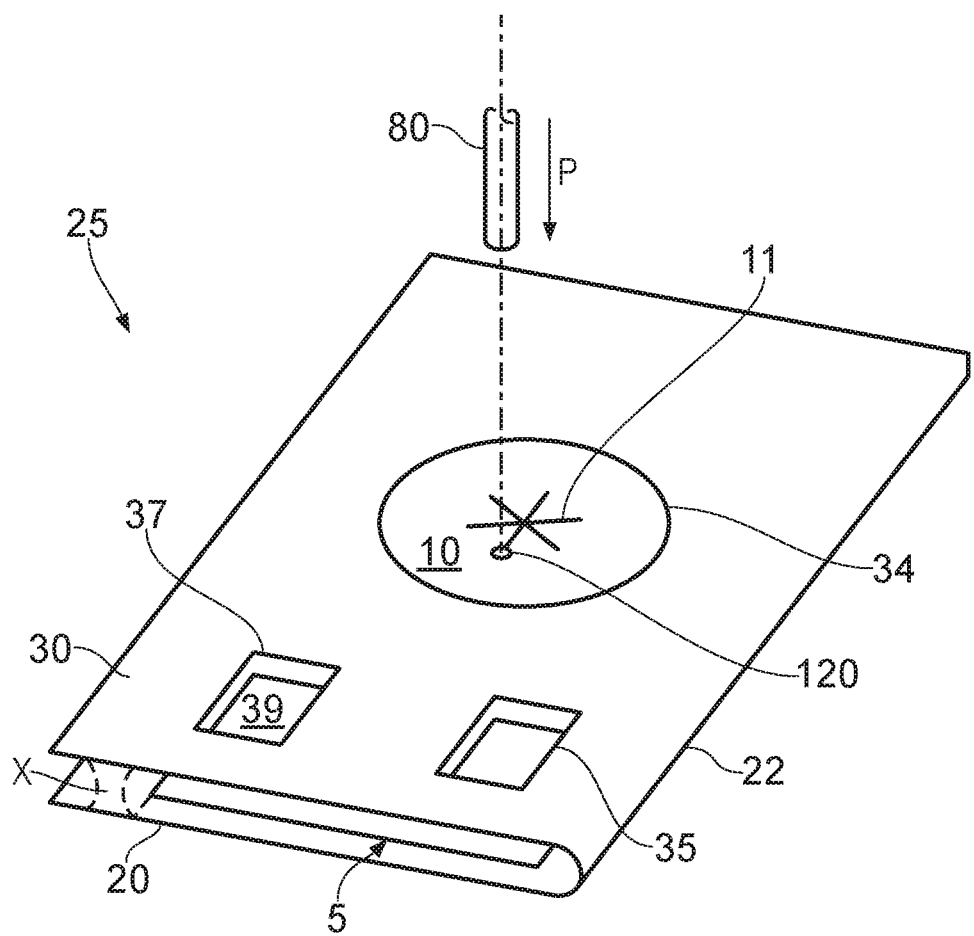
FIG. 6 shows a portion of the sample receiver separated from the remainder of the receiver, for further processing.

The envelope 25 now separated and containing the sample storage medium 10 is shown in FIG. 6, ready to have a portion 120 of the medium 10 removed for analysis, for example by means of a punch 80 which is forced in the direction of arrow P to cut through the medium 10 which is exposed on both sides at opposed windows 24 and 34. The punched portion 120 can be processed according to known techniques to obtain a characterisation of any DNA present thereon, for example Short Tandem Repeat (STR) analysis.

In order to calibrate an automated system, the opening 34 can be supplemented with a secondary opening, in the form of an additional window 35 used to view the underlying medium 10 in order to automatically determine the format, for example the unadulterated colour, of medium 10 using a camera based system. The opening 34 can then be more easily found by automated means. Also, for cleaning the punch 80 between taking samples, a cleaning zone can be provided in the form clean area 39 on the sample storage medium 10 accessed via a further window 37. In use the punch 80 can, effectively, be wiped between successive punching operations by punching in the clean area 39. Each of the window openings 35 and 37 are through-openings such that opposed openings 25 and 27 (FIG. 1) are folded into register with the openings 35 and 37 respectively.

It will be appreciated that the drawings show and exaggerated gap between adjacent folded features of the receiver 100, for illustration purposes, but in practice the receiver 100 is relatively thin, being formed of just 6 (in this instance) layers of sheet material such as paper or thin card, folded together and lying against each other. Other materials could be used, to make a thinner receiver, for example sheet polymer materials, for example polyethylene for the blank 15, and a fibrous or etched polymer sample storage medium 10, such as a polyamide with a flocked surface.

It will be appreciated that the manufacture of the above mentioned device can be performed by hand, or by machine. Automated machine manufacture is preferred because there is less risk of contaminating the device with human DNA. Thus, a substantially human DNA free manufacturing environment is preferred. As an alternative, or as well as, the components of the sample receiving device or the finished device can be exposed to Ethylene Oxide (EtO) gas of sufficient concentration to render human DNA unamplifiable by means of any polymerase chain reaction (PCR), and thereby to negate any potential human DNA contamination.

Although one embodiment has been described and illustrated, it will be apparent to the skilled addressee that additions, omissions and modifications are possible to those embodiments without departing from the scope of the invention claimed. For example, a rectangular outer receiver shape is shown, but other shapes are possible. Windows 24,25,27, 34,35,37 and 44, and cut-outs 46,56 and 66 could be different shapes to those illustrated.

The invention claimed is:

1. A biological sample receiver comprising:
    a planar substrate for receiving a biological sample including a surface area for accepting a biological sample;
    an envelope substantially surrounding the substrate, said envelope including an opening for facilitating the deposit of a biological sample onto said surface area; and
    a protective cover formed around the envelope said protective cover including a closure panel moveable at least to a first position where the opening of the envelope is at least partially concealed, and to a second position where the opening is exposed at least sufficiently to allow said deposit;
    the device being characterised in that said envelope and said cover are formed from a single sheet of folded material, wherein said single sheet includes a weakness between portions of the sheet used to form the envelope and portions of the sheet used to form the protective cover, and wherein said weakness is configured to allow the slidable separation of the envelope from the cover.

2. The biological sample receiver of claim 1, wherein said weakness is in the form of perforations.

3. The biological sample receiver as claimed in claim 2, wherein said single sheet of folded material includes a first panel and a second panel foldable together at a first fold to form said envelope.

4. The biological sample receiver as of claim 3, wherein said protective cover includes a third panel connected to one of the first or second panels at a second fold which includes said weakness and a fourth panel connected to the third panel at a third fold between the third and fourth panels, the third fold being spaced from the second fold, and wherein the closure panel is connected to the fourth panel at a fourth fold between the fourth panel and closure panel, the fourth fold being spaced from the third fold.

5. The biological sample receiver of claim 4, wherein the second, third and fourth folds are generally parallel to each other and the cover has at least one open end configured to allow the envelope to be slid out of the open end of the cover.

6. The biological sample receiver of claim 4, wherein each panel of the cover includes a finger-size opening.

7. The biological sample receiver of claim 3, wherein the first and second panels have edges which are fixed.

8. The biological sample receiver of claim 7, wherein the edges of the first and second panels are fixed by means of adhesive to form said envelope.

9. The biological sample receiver of claim 1, wherein said cover includes at least two aligned finger-size openings which are configured to allow gripping of the envelope on opposed sides of said envelope.

10. A method for manufacturing the biological sample receiver of claim 1, the method comprising, in any suitable order, the steps of:
   a) forming a blank of sheet material;
   b) forming first, second, panels in an envelope portion of the sheet material, the first and second panels being divided at a first fold line;
   c) forming third, fourth and cover panels in the remaining portion of the sheet material, each divided by further fold lines, and divided from the first and second panels by a weakened part of the sheet material;
   d) providing a planar biological sample receiving medium;
   e) forming an envelope by folding the first and second panels to substantially enclose the medium;
   f) folding the third, fourth and cover panels at the further fold lines to substantial surround the envelope.

11. The method as of claim 10, further including the step of forming openings in at least the third panel and one of the first or second panels for exposing the medium in the envelope.

12. The method of claim 10, wherein the method is carried out in a substantially human DNA-free environment.

13. The method of claim 10, further including the step of exposing the biological sample receiver or any part thereof to Ethylene Oxide gas to render human DNA unamplifiable by means of any polymerase chain reaction (PCR).

14. The biological sample receiver of claim 1, wherein envelope substantially surrounds the substrate.

15. A biological sample receiver comprising:
   a planar substrate for receiving a biological sample including a surface area for accepting a biological sample;
   an envelope at least partially surrounding the substrate, wherein said envelope includes at least a first panel, the first panel including an opening for facilitating the deposit of a biological sample onto said surface area; and
   a protective cover formed around the envelope, said protective cover including a third panel, a fourth panel, and a closure panel, the protective cover moveable at least to a first position where the opening is at least partially concealed and to a second position where the opening is exposed at least sufficiently to allow said deposit;
   the device being characterised in that the first panel, the third panel, the fourth panel, and the closure panel are formed from a single sheet of folded material, with the third panel being connected to the first panel at a second fold, the fourth panel being connected to the third panel at a third fold between the third and fourth panels, the third fold being spaced from the second fold, and the closure panel being connected to the fourth panel at a fourth fold between the fourth panel and closure panel, the fourth fold being spaced form the third fold,
   wherein the second fold includes a weakness configured to allow the slidable separation of the first panel from the third panel.

16. The biological sample receiver of claim 15, wherein said weakness is in the form of perforations.

17. The biological sample receiver of claim 15, wherein said envelope includes the first panel and a second panel connected to the first panel to form said envelope and wherein the envelope substantially surrounds the substrate.

18. The biological sample receiver of claim 17, wherein the second panel is connected to the first panel at a first fold.

* * * * *